United States Patent [19]

Laing

[11] Patent Number: 5,059,182
[45] Date of Patent: Oct. 22, 1991

[54] PORTABLE INFUSION DEVICE

[75] Inventor: David H. Laing, 16A Henry Street, Toronto, Ontario, Canada, M5T 1X1

[73] Assignee: David H. Laing, Toronto, Canada

[21] Appl. No.: 352,296

[22] Filed: May 16, 1989

[30] Foreign Application Priority Data

Apr. 12, 1989 [CA] Canada .................................. 596541

[51] Int. Cl.⁵ .............................................. A61H 5/00
[52] U.S. Cl. .................................... 604/142; 604/141; 222/95
[58] Field of Search ............... 604/131, 134, 140, 141, 604/142; 222/94, 95

[56] References Cited

U.S. PATENT DOCUMENTS

| | | | |
|---|---|---|---|
| 2,766,907 | 10/1956 | Wallace, Jr. | 604/141 |
| 4,267,834 | 5/1981 | Barger et al. | 604/250 |
| 4,507,116 | 3/1985 | Leibinsohn | 604/142 |
| 4,626,243 | 12/1986 | Singh et al. | 604/141 |
| 4,735,613 | 4/1988 | Bellin et al. | 604/142 |

FOREIGN PATENT DOCUMENTS 2041756 9/1980 United Kingdom .

OTHER PUBLICATIONS

Advertisement—Life Med Technologies Inc.—Quality Products for Medical Professionals—Copyright 1985.

Primary Examiner—C. Fred Rosenbaum
Assistant Examiner—Corrine Maglione
Attorney, Agent, or Firm—Ivor M. Hughes

[57] ABSTRACT

A portable infusion device which can be user operated almost anywhere for administration of a solution at a substantially steady flow rate from storage, the device comprising in combination a flow restrictor and a propulsion system using a pressure medium carried in a flexible extendible container for causing the solution to be administered to a patient at a substantially steady rate of flow through the flow restrictor.

17 Claims, 9 Drawing Sheets

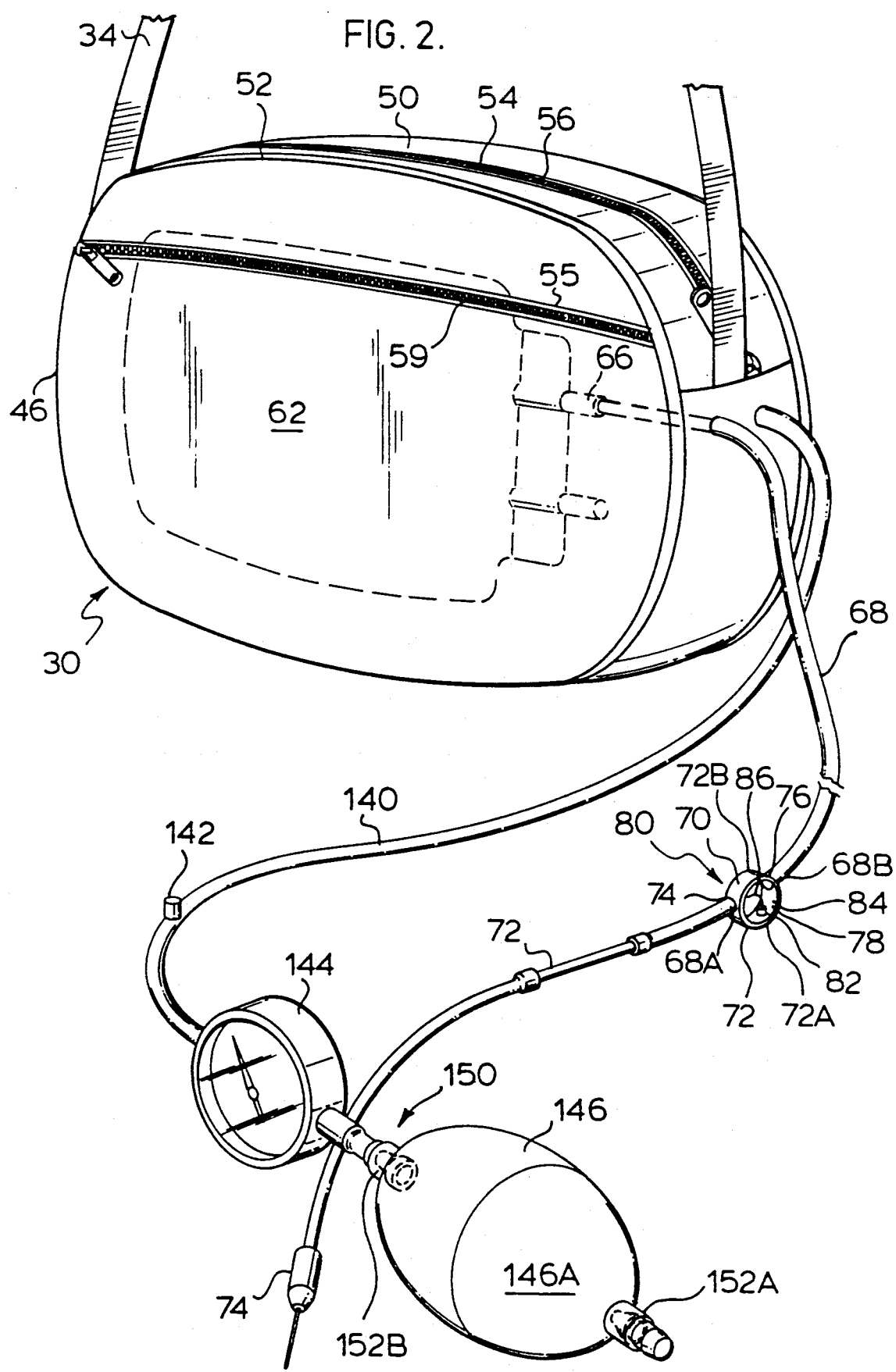

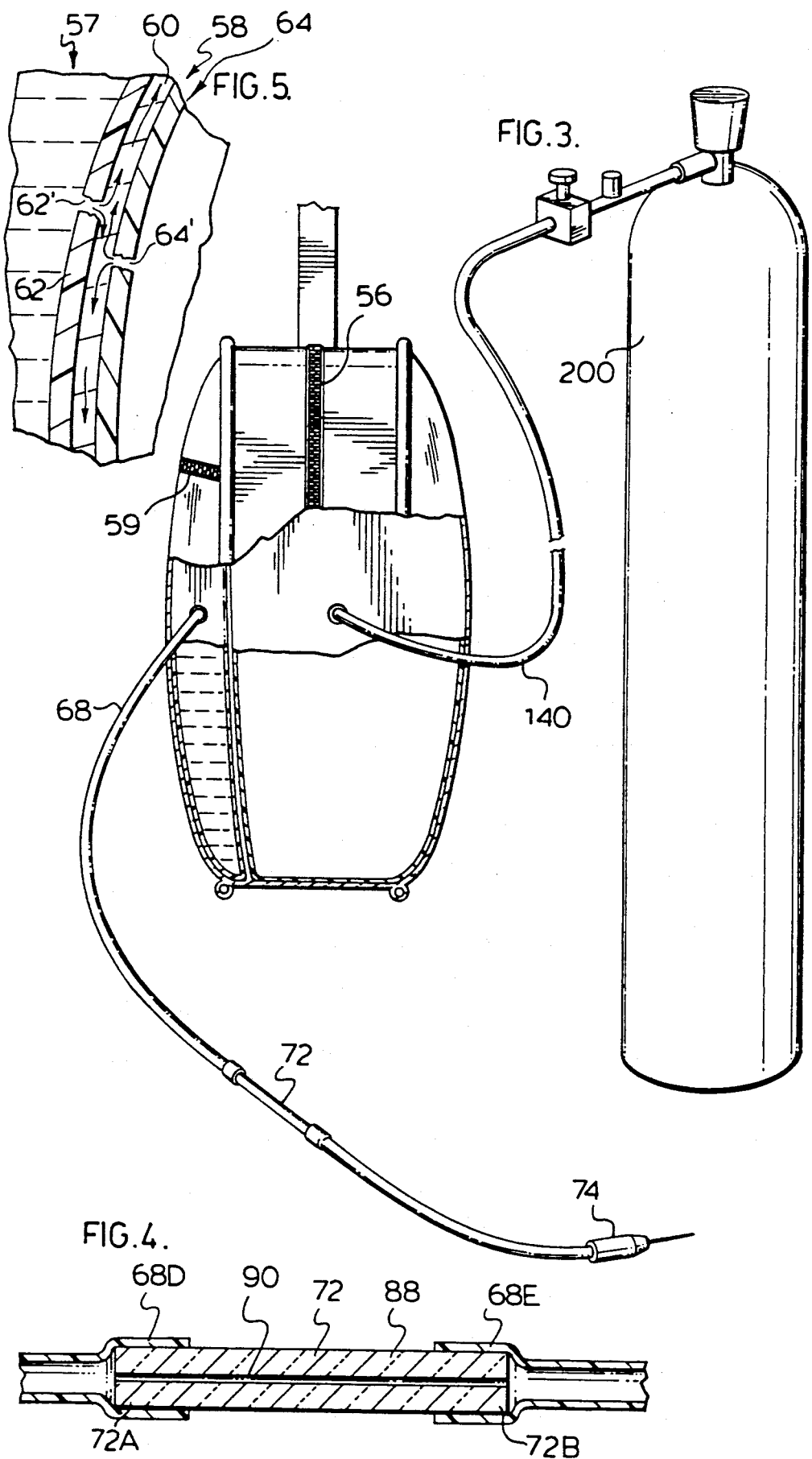

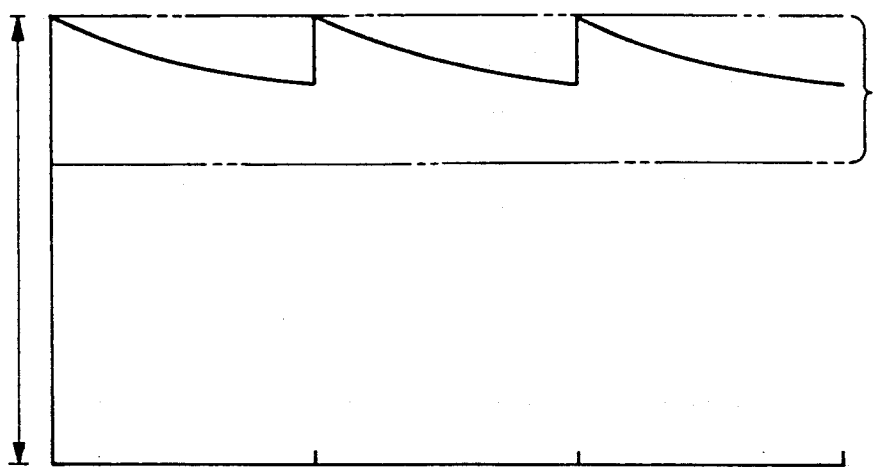
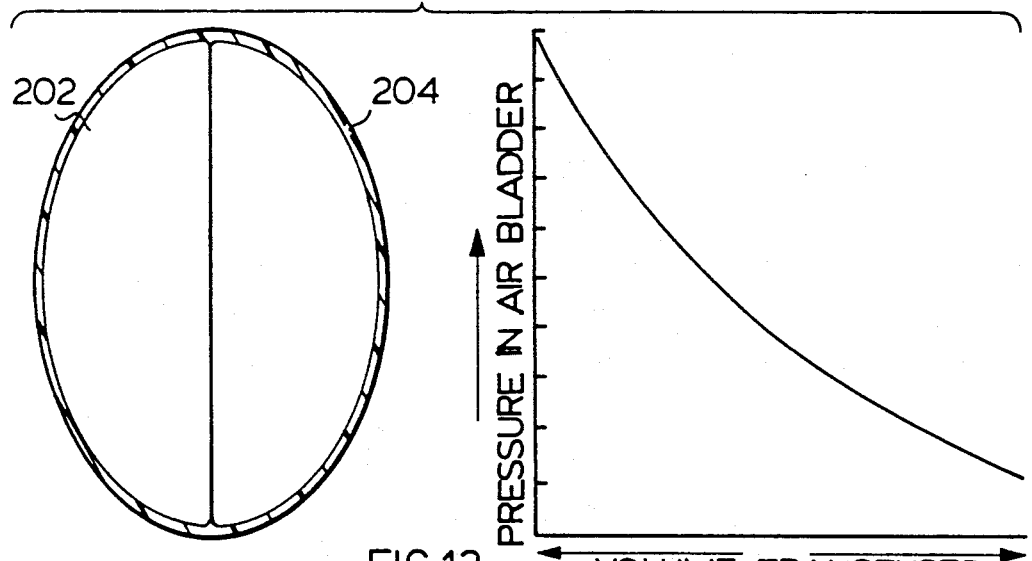
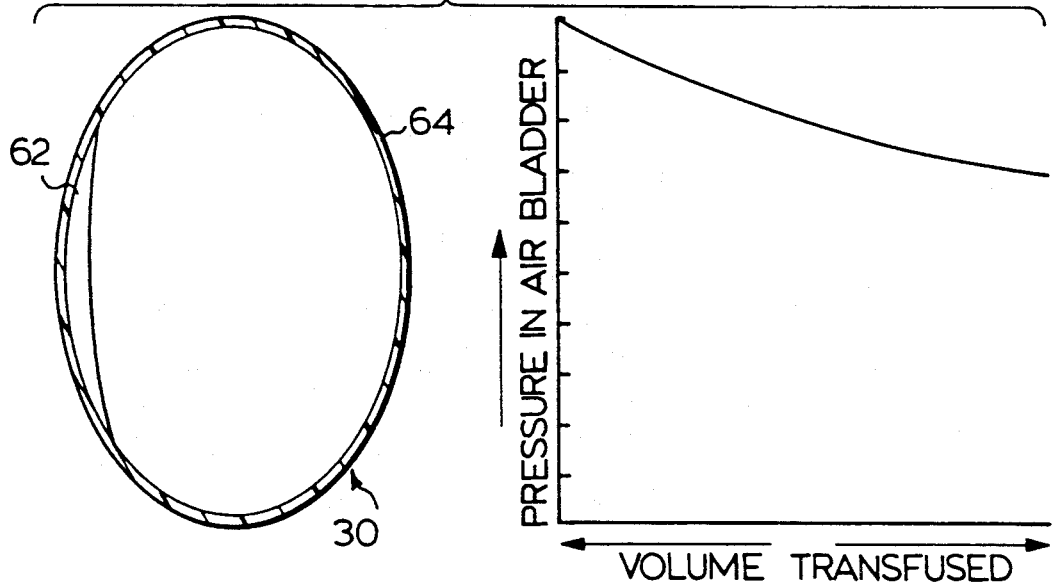

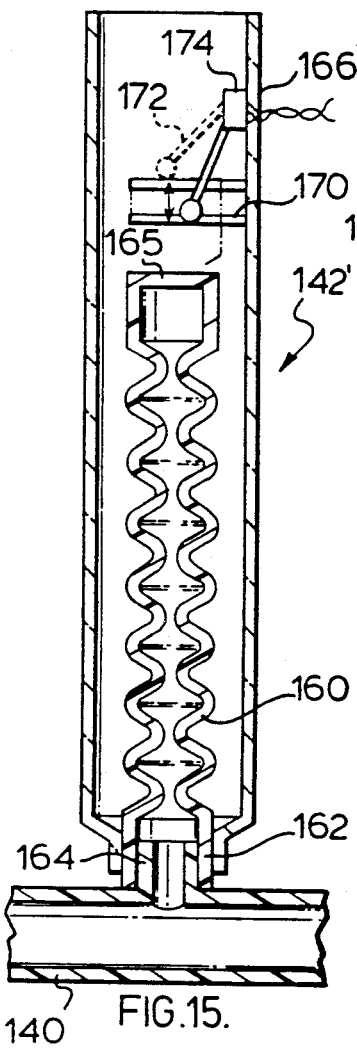 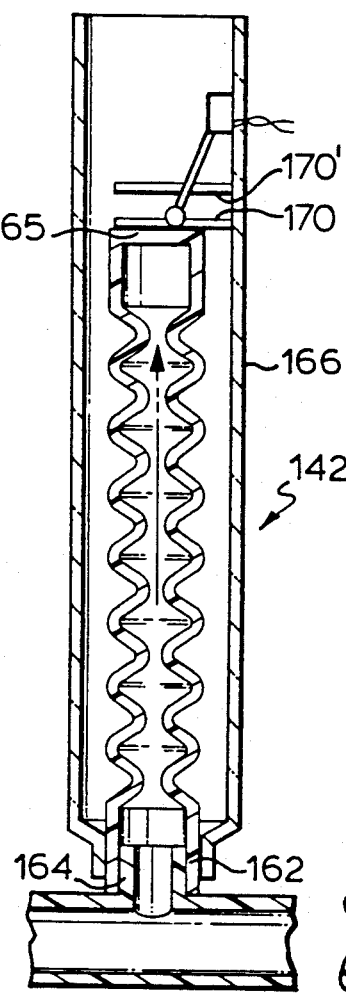 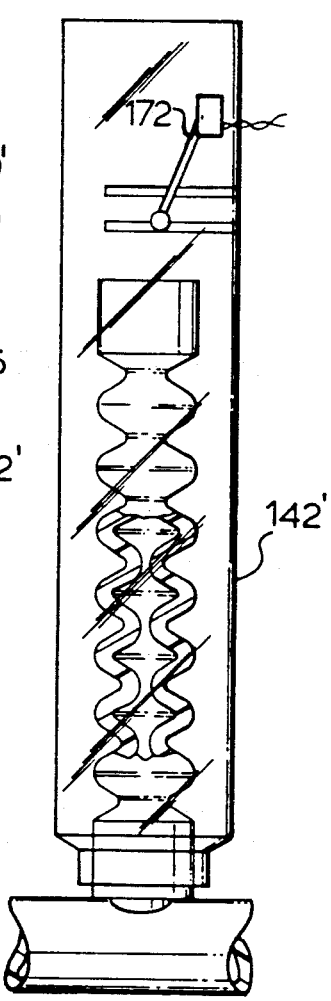
FIG.15.   FIG.16.   FIG.17.
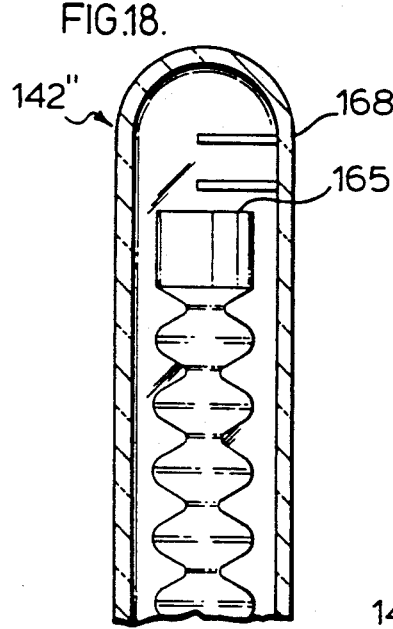 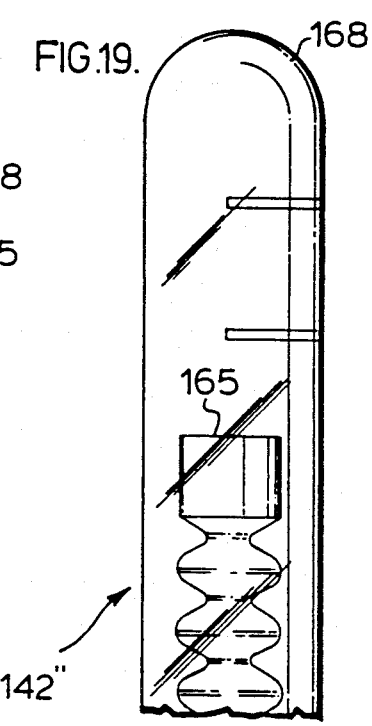 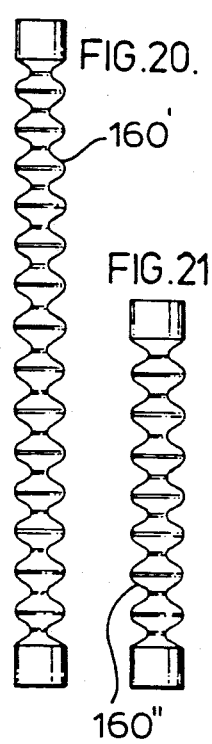 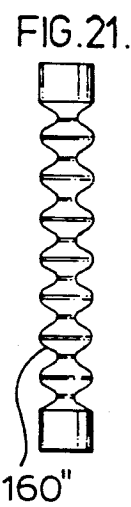
FIG.18.   FIG.19.   FIG.20.   FIG.21.

PORTABLE INFUSION DEVICE

FIELD OF INVENTION

This invention relates to portable infusion devices and components suitable for use therewith and particularly to infusion devices having continuous rates of flow.

BACKGROUND OF THE INVENTION

In the Dec. 3, 1988 edition of the Globe & Mail newspaper published in Toronto, Ontario, Canada, there appeared the following advertisement:

PLEASE DON'T TAKE MY PUMP AWAY

The W. Gifford-Jones Foundation recently received this letter from the Louise Marshall Hospital in Mount Forest, Ontario. We think the letter speaks for itself.

Dear Dr. Gifford-Jones

The Louise Marshall Hospital, Mount Forest, Ontario, is a 37 bed active hospital serving an area of 12 thousand people. Our first contact with the subcutaneous infusion pump occurred six months ago when we had to borrow a pump from another hospital for a patient who was dying from terminal cancer. We now have another patient utilizing the pump, again on loan. In both cases the pump has allowed more independence and pain-free existence. The patient's statement, "I hope you don't take this pump away from me" expresses the feelings and need clearly. We would deeply appreciate it if the Gifford-Jones Foundation could donate a pump to this hospital.

The Foundation purchased a computerized pump the size of a cassette tape recorder for the Louise Marshall Hospital. The pump delivers continuous doses of painkillers into subcutaneous tissues. This provides round-the-clock relief of pain and patients can often be discharged home to family. The pumps cost $3,500.00. We wish we had the funds to purchase one this Christmas for every Canadian hospital.

CAN YOU THINK OF A BETTER CHRISTMAS GIFT?

Bionica Pty Ltd. produces and markets the "Bionica MDS110" (E.M.) infusion pump, a battery operated micro computer controlled infusion pump operated by a miniaturized motor coupled to a reduction gearbox for developing substantial output torque and delivering an intermittent flow cf 0-995 microliters/hour in 5 microliter/hour steps of medication. The infusion pump utilizes a standard 10 ml. syringe as a reservoir for the medication and uses the syringe's plunger to displace the medication at a predetermined and pre-programmed rate. The cost of the pump is about $4,000.00 (Canadian).

An attempt to produce an infusion pump providing a continuous rate of flow was made with the IMED 927 (t.m.) volumetric infusion pump. However, the pump suffers accuracy problems when the flow rate is less than about 20 c.c. of medication/hour.

Because it is not financially possible to provide electrically operated and controlled rate infusion pumps for every patient, gravity drip infusion devices have been used to permit fluid medication to flow by gravity into a vein or artery of a patient. However, monitoring use of the gravity drip infusion devices requires substantial amounts of nurses' time frequently. These devices are unreliable. Where too rapid infusion of the medicine occurs with the gravity drip infusion devices, patients have died. In this regard, Applicant believes about 1,000 patients a year die from improper infusion of medicine—for example, KCl overdosing of persons with cardiac problems using these devices.

Pressure infusion apparatus have been proposed which purportedly deliver medicine under pressure to a patient.

U.S. Pat. No. 2,766,907 purports to disclose apparatus for intravenous injection of solutions under controlled pressure. Container 10, made of flexible, substantially inextensible walls, is divided into two compartments separated by flexible, substantially inextensible flap 28, one compartment for holding a standard flexible, collapsible receptacle or bag filled with the liquid medication to be infused. Bladder 22 is expansible having walls of elastic rubbery material. Two connecting tubes 24 and 26 serve the functions of inflation and deflation of the bladder and positioning bladder 22 in container 10.

In use of container 10, bladder 22 is purportedly inflated to the desired pressure (See gauge 32) to exert the desired pressure on receptacle 18. As liquid medication purportedly leaves bag 18 through outlet 20, the pressure in the bladder rapidly decreases. Because the volume of bladder 22 appears to be less than the volume of bag 18, the pressure exerted by the bladder rapidly decreases and thus the bag if elevated soon discharges only by gravity unless "repumped". Furthermore, because container 10 comprises flexible inextensible walls, it cannot exert stored elastic energy on the liquid medication filled bag.

In U.S. Pat. No. 3,153,414, an apparatus is provided for the induced infusion of liquid medication from a flexible container having an inflatable bladder and a sleeve encircling the bladder. The bladder surrounds a liquid medication filled container 11. The bladder may be filled by hand inflation bulb 31 through fitment 30. The bladder is designed to rupture at a fluid pressure which is less than the fluid pressure at which container 11 will rupture. The example given is 8 pounds per square inch—a not insubstantial pressure. The patent describes the device's purported use at column 3, line 18 as follows:

"In use, the liquid container 11 is inserted into the opening 29 defined by the inner wall 23 of the bladder 22. The handle 17 of the apparatus 10 is passed through the elongated slot 15 in the flexible liquid container 11 and is then hooked over the supporting arm 18. The intravenous needle 12C is inserted into the patient when the infusion of the liquid is required. When it is desired to induce the infusion of the liquid contained in the liquid container 11, the hand operated bulb 31 or its equivalent is actuated to inflate the bladder 22. As the pressure in the bladder 22 increases the liquid contained in the liquid container 11 will be induced through the tubing 12 and the intravenous needle 14 into the patient.

In the event that excessive pressure is built up within the bladder 22, the bladder 22 will rupture, and in fact, the bladder will rupture before the liquid container 11 ruptures."

Because the container is flexible, no pressure can be exerted on the bladder until the cross-section of the bladder takes up a "circular" disposition. However, no such disposition is disclosed in the patent. Nor is any mention made of the use of extendibility of the container wall to store elastic energy. Therefore, this proposal does not provide substantially constant pressure over a period of time by the bladder on the liquid medication filled container 11. In fact, the difference between the effective volumes of the liquid medication filled container 11 and bladder 22 is not substantial.

Further, neither of the proposals in the two patents make any attempt to control the rates of flow and minimize the pressure employed. Neither do such proposals eliminate back flow of blood, nor address the problem of needle obstruction at the injection site.

Applicant is aware of other references relating to other proposals for devices. These are:

| U.S. Pat. No. | Title |
| --- | --- |
| 3,780,732 | NON-GRAVITATIONAL INFUSION SET |
| 3,228,395 | BLOOD BAG TRANSFUSION UNIT WITH PRESSURE CHAMBER |
| 4,090,514 | PRESSURE INFUSION DEVICE |

Applicant is also aware of the "Travenol Infusor", a product of Travenol Laboratories, Inc.

The "Travenol Infusor" consists of a housing and balloon reservoir in communication with a controlled size orifice (flow restrictor), purportedly regulating the infusion at a constant rate. The balloon is filled with medicine stretching the balloon membrane of the reservoir. The advertising literature states that the infusor purportedly provides a flow at a reliable and constant rate of 2 ml./hr. The infusor, however, does not provide such steady rate for the contents of the infusor. The starting pressure increases as the volume of drug is discharged from the balloon reservoir and drops to zero when the volume of drug is discharged.

Thus the rate of discharge is not constant. Where it is important in the administration of a drug to keep the flow rate into the patient constant this device is not practical. Additionally because of the high initial pressure (9 psi) and the low flow rate, the opening through the reservoir is about $0.0008\mu$. Thus a problem of particulate matter blocking the orifice, arises.

It is therefore a object of this invention to provide a portable infusion device which overcomes the deficiencies of the prior art devices.

It is a further object of this invention to provide such device which is fully reliable and of minimum cost.

It is a further object of the invention to provide components for such portable infusion device.

Further and other objects of the invention will be realized by those skilled in the art from the following summary of the invention and detailed description of embodiments thereof.

SUMMARY OF THE INVENTION

At its broadest, this invention relates to a portable infusion device which can be user operated almost anywhere for administration of a solution substantially steady flow rate from storage, the device comprising in combination a flow restrictor and a propulsion system using a pressure medium carried in a flexible extendible (extensible) container for causing the solution to be administered to a patient through the flow restrictor (of, for example, varying length and diameter or cross-section) to provide a steady rate of flow of the solution into the patient.

According to another aspect of the invention, a portable infusion device is provided for administration of a solution (for example, liquid medication) at a substantially steady flow rate from storage, the device comprising a housing enclosing a predetermined volume, the housing for receiving a reservoir of the solution to be administered under pressure, and a pressure bladder comprising a flexible extensible (extendible) container for carrying a pressure medium, the pressure bladder when pressurized being in intimate pressure contact in the housing with the reservoir. In one embodiment the outlet of the reservoir carries a flow restrictor.

According to an aspect of the invention a portable infusion device is provided for administration of a solution (for example, liquid medication) at a steady flow rate from storage (for example, a bag having a carrying strap, (e.g. shoulder strap)), the device comprising a housing enclosing a predetermined volume, at least one opening through the housing into the volume (and preferably means for closing the at least one opening), the housing being of flexible and extendible (extensible—being stretchable to some extent) material and also preferably being of leak resistant material, a pressure (for example, air) bladder for being carried within the volume of the housing (in intimate contact with a reservoir for the solution to be administered), the (air) bladder being inflatable within the housing and comprising flexible extendible material, the bladder preferably being of flexible and extendible (extensible) material], the (air) bladder comprising an (air) inlet for introducing the pressure medium (for example, air) into the bladder for inflating the bladder to a predetermined pressure (preferably carrying a one way valve for introducing the pressure medium), pressure release means (e.g. pressure relief (release) valve) in communication with the contents of the pressure bladder to ensure the predetermined pressure is maintained and excess pressure is released, the volume of the housing also for receiving the reservoir containing the solution to be administered (for example, an I.V. bag), the reservoir being made of flexible material, an outlet from the reservoir for administering the solution, for example, through a needle to a patient, the outlet comprising a flow restrictor (for example, a predetermined length of glass tube having a precise opening therethrough (for example, an opening of 0.007" ($\pm 0.0001$")) through the length of the glass tube manufactured by Accu-Glass Division of Becton Dickinson, 10765 Trenton Avenue, St. Louis, Mo., 63132), the volume of the bladder being at least about five times the volume of the reservoir.

In another embodiment the flow restrictor may comprise a helical opening spiralling from one end of a plastic or glass tube to the other. In another embodiment, the inlet for introducing the pressure medium, for example the one way valve may be connected to a pressure pump, hand pump, machine pump, or computer controlled machine pump or any other means for filling the bladder to the desired pressure.

Pressure Indicating means or Pressure Indicator may be provided for displaying the pressure in the bladder. In one embodiment, an inexpensive pressure indicator may comprise a bellows (for example, thick wall corrugated rubber bellows [which holds its shape]) carried within a tube, one end of the bellows in communication with the medium whose pressure is to be measured, for example, bladder, the other end closed, the tube preferably carrying indicia for indicating the pressure of the pressure medium within the bladder. The tube of the pressure indicator means may be closed or open at the end of the tube on the side of the closed end of the bellows remote from the end of the bellows in communication with the pressure medium (for example, bladder). If the end of the tube is closed, the indicator or indicating means may be used to measure high pressure. If the end of the tube is open, the indicator or indicating means may be used to measure lower pressure.

In use, in one embodiment the rubber bellows in the indicator is caused to expand by the pressure in the bladder. If the ends of two tubes are closed and two indicators provided, one in one tube end having double the volume of the other tube end between the closed end of the tube and bellows, the accuracy of the indicator is doubled in the indicator having the end having double the volume between the closed end and bellows. The tube may carry a microswitch (secured to a buzzer) between the closed end of the bellows and open or closed end of the tube for indication by the buzzer when a toggle arm attached to the microswitch indicates (as for example by falling as the closed end of the bellows falls), the pressure falls below a predetermined pressure to a lower predetermined pressure where repressurizing is required.

In another embodiment, the volume in the housing may be lined by porous material (air permeable material). In another embodiment the at least one opening through the housing may be closed by a zipper.

In another embodiment, the volume in the housing may be divided into two compartments and the two compartments may be separated by, for example, air permeable material to provide a bladder receiving compartment of the housing and drug reservoir compartment, the portions separated by the air permeable material.

From the above, it is apparent that infusion devices manufactured in accordance with the invention can be manufactured inexpensively.

According to another embodiment of the invention a flow indicator (for example, a thin strand of material secured in a transparent body) may be secured in communication with the outlet from the reservoir for the passage of solution therethrough.

In another embodiment, the pressure relief valve may comprise a whistle for whistling when excess pressure is released.

The pressure relief valve and the preferably one way valve for introducing the pressure medium into the pressure bladder may be the same valve, a bi-directional relief valve manufactured by Vernay Laboratories, Inc., of Yellow Spring, Ohio, in accordance with U.S. Pat. No. 4,341,239 and/or U.S. Pat. No. 4,434,810.

The valve may be a one-piece molded, leak-proof elastomeric component that has design capabilities of opening at various pressures and flowing in one direction at a predetermined cracking pressure and flowing in the opposite direction at a different cracking pressure.

Relief pressures ranging from 0.25 psi to 60 psi, in either direction can be designed into the product.

The pressure bladder may be pressurized to 2 ½ psi [vein pressure is between about 0 psi and about ½ psi]. Thus in use of the infusion device, sufficient pressure is provided to cause solution to flow through the needle into the vein. If a blockage exists on the needle [piece of skin or tissue], the extra pressure on the solution from the air bladder will remove the blockage.

Where the air bladder is flexible and the housing of flexible and extendible material and when the inflation of the bladder causes the housing material to extend (stretch to some extent), as the solution first flows from the reservoir, the material of the housing first restores. Thus the pressure exerted by the pressure bladder first does not change substantially. Thereafter, as further solution flows from the reservoir, the pressure in the bladder slowly reduces. For example, the pressure in a 3500 c.c. pressure bladder used in association with a 300 c.c. reservoir, will first stay substantially the same and then fall slowly from 100 mm. to 70 mm. [Where both the reservoir and pressure bladder are of the same volume of, for example, 300 c.c., the pressure in the pressure bladder would quickly drop from 100 mm. to 10 mm as the solution flows from the reservoir (without emptying the contents of the reservoir)].

In another embodiment, the thickness of the pressure bladder wall is such that it requires only 1 mm. of Hg pressure to inflate it to the desired volume in the housing (outer bag) (so as to minimize the pressure drop from the pressure bladder to the reservoir, that is, to minimize the loss of pressure on the solution (drug)); the pressure to inflate the housing in this embodiment is 100 mm. of Hg. Because the effective driving force on the flow restrictor remains substantially constant, there is no need for "repumping" with for example, a ball pump over the length of the infusion of, for example, 200 c.c. of drug.

Where there is concern of blood back flow, a one way valve may be provided proximate the needle in the outlet (for example, outlet tube) between the reservoir at the injection site.

The housing and/or pressure bladder may be of any suitable material exhibiting the desired characteristics. Two such materials may be vinyl and artificial rubber.

BRIEF DESCRIPTION OF THE DRAWINGS

The invention will now be illustrated with respect to the following drawings illustrating embodiments of the invention in which:

FIG. 2 is a close-up perspective view of the portable infusion device of claim 1.

FIG. 3 is an end view of the portable infusion device in FIGS. 1 and 2, partly in cross-section being pressurized according to one embodiment of the invention.

FIG. 4 is a close-up cross-sectional view of one component (flow-restrictor) of the device shown in FIGS. 1, 2 and 3.

FIG. 5 is a close up cross-sectional view of part of the structure of the embodiment shown in FIGS. 1, 2 and 3.

FIGS. 12 and 13 illustrate graphically the pressure drops of the pressure bladders of two devices as medicine is infused from the devices, the device of FIG. 13 being constructed according to an embodiment of the invention.

FIG. 14 illustrates graphically the pressure drops using the device in FIG. 13 and the repressurization of the pressure bladder.

FIGS. 15 through 21 inclusive illustrate pressure indicators according to embodiments.

DETAILED DESCRIPTION OF EMBODIMENTS

Figure 1:
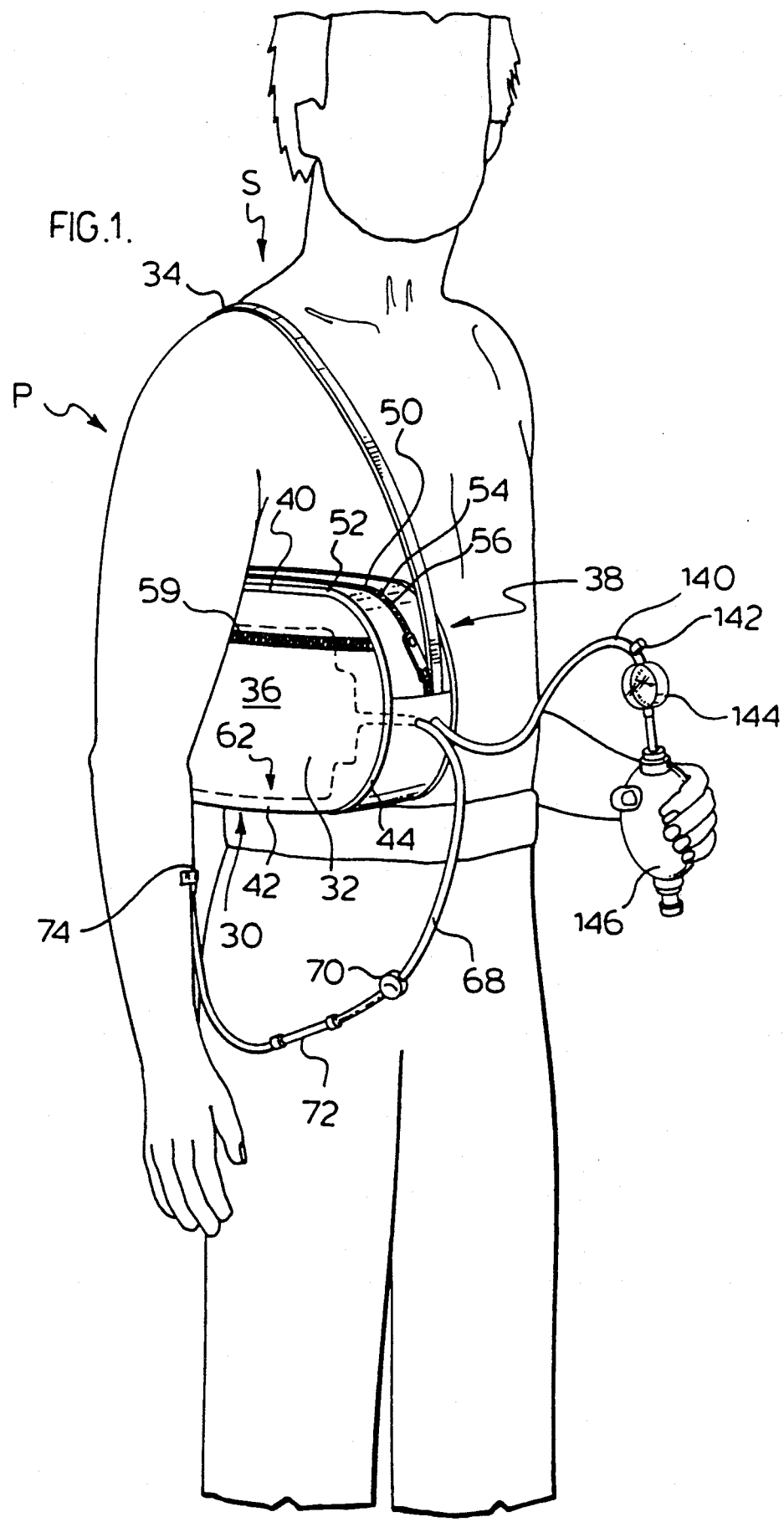
FIG. 1 is a perspective view of a patient using a portable infusion device according to an embodiment of the invention.

With reference to FIG. 1, patient P carries portable infusion device 30 comprising shoulder bag 32 having carrying strap 34 over shoulder S of Patient P. Shoulder bag 32 comprises end panels 36 and 38 each panel comprising parallel spaced side edges 40 and 42 joined by semi-circular end portions 44 and 48. Each of the panels are sewn to continuous loop 50 of material of the same shape as each panel 36 and 38. Piping or 52 is sewn with the panels and loop to strengthen the joint. Each of the panels 36, 38 and semi-circular portions 44 and 48 is made of flexible and extensible (extendible) vinyl material. Openings 54 and 55 are closed by zippers and 56 and 59 are respectively provided for access into the interior of shoulder bag 30. Bag 30 is lined on the inside by, and divided into two compartments by, air permeable material 60 (see FIG. 5). Compartment 57 leading from opening 55 is provided for holding an Intravenous (I.V.) bag 62 (reservoir) containing solution (medicinal) to be administered under pressure to a patient at a constant flow rate. Compartment 58 leading from opening 54 is provided to hold air pressure bladder 64 made of flexible and extensible (extendible) material. Bag 62 carries 300 c.c. solution. Pressure bladder 64 has an inflated pressure volume of 3,000 c.c. of air.

Bag 62 is secured by outlet 66 to tube 68 extending from bag 30. Tube 68 carries flow indicator 70 (for indicating that solution is flowing from Intravenous bag 62), flow-restrictor 72 and terminating in needle 74 (for injecting into patient P [see FIG. 1]).

Flow indicator 70 comprises annular shaped wall carrying opposing openings 74 and 76 for securing cut ends 68A and 68B respectively of tube 68. Wall 72 supports disks 78 and 80 at edges 72A and 72B. Disks 78 and 80 are each transparent. Raised Boss 82 is supported on the inside surface 84 of annular wall 72. Flexible plastic thin strand 86 is secured to boss 82 and is bent downstream by the flow of solution passing through tube 68 through flow indicator 70.

Flow restrictor 72 is a length of glass tubing 88 2" (about 5 cm) in length having precise bore (opening) 90 of 0.007" (±0.0001") through the length of the glass tubing. The control of the length of tubing and size of the bore opening will determine the flow of solution through tube 68 to needle 74. Restrictor 72 is inserted into tube 68 by stretching portions 68D and 68E over the ends 72A and 72B respectively of tubing 72.

Figure 6:
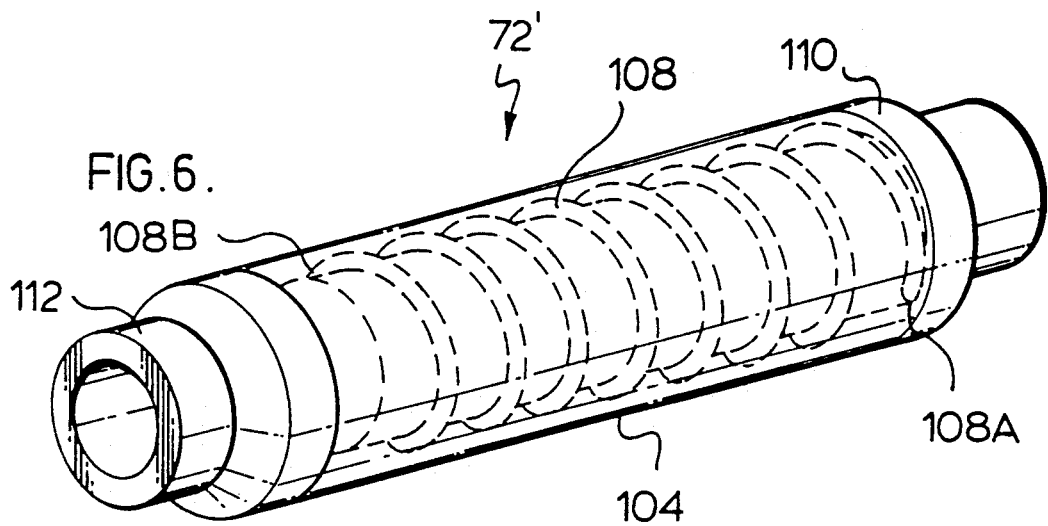
FIG. 6 is a perspective view of another flow restrictor suitable for use with the embodiment shown in FIGS. 1, 2 and 3.
Figure 11:
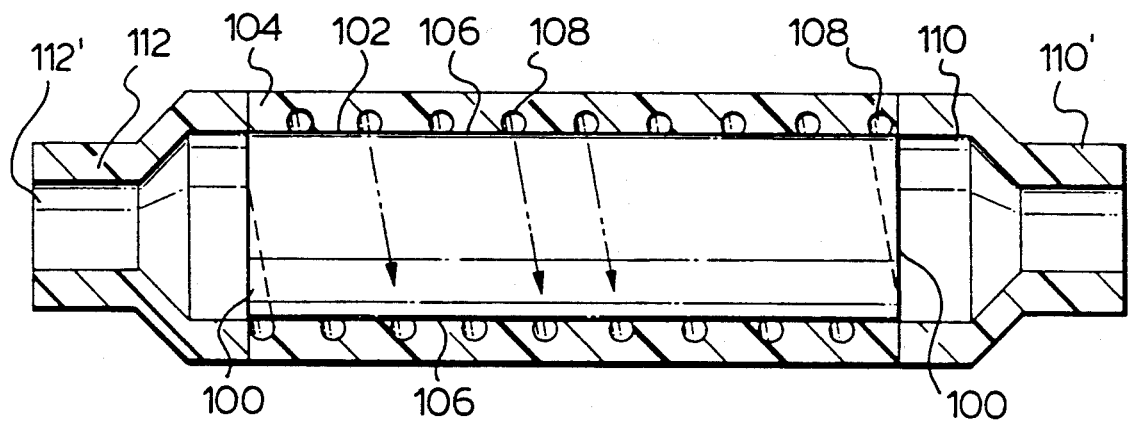
FIG. 11 is a cross-sectional view illustrating the assembly of the component shown in FIG. 10 with another component used to form part of the structure forming the flow restrictor in FIG. 6.
Figure 22:
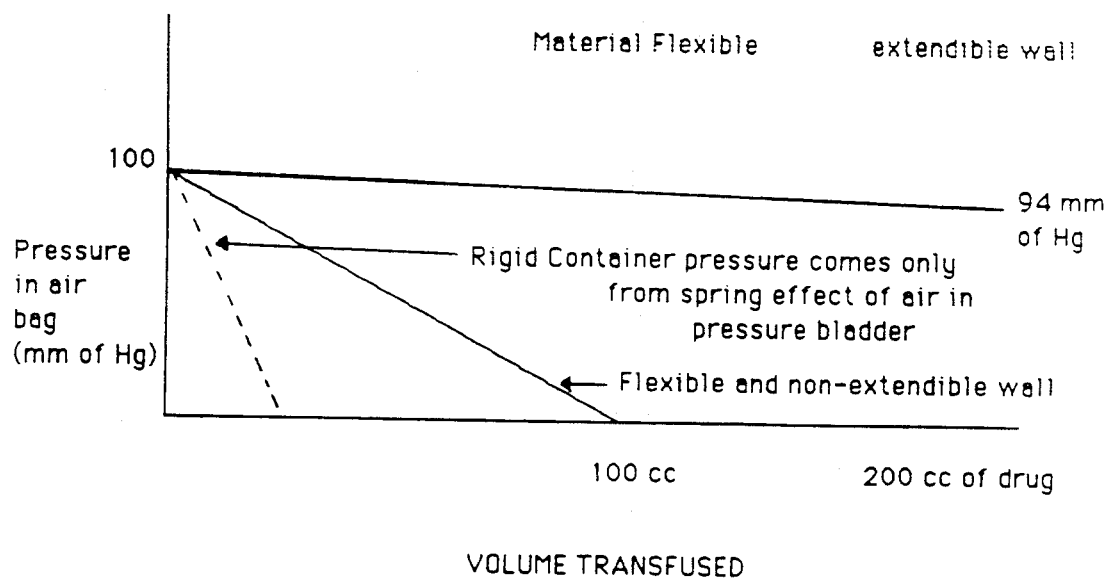
FIGS. 22 and 23 are graphs which illustrate the differences in the pressure where the material used is flexible and extendible versus flexible and nonextendible.
Figure 23:
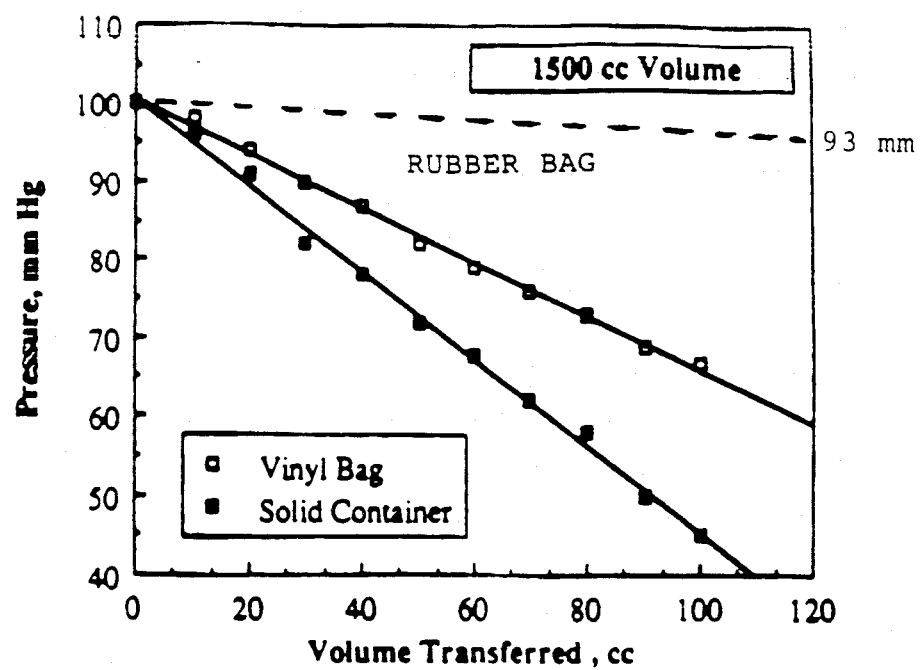

An alternate flow restrictor 72' is shown in FIG. 6 and 11. Flow restrictor 72' comprises cylindrical core 100 having outer wall 102 surrounded by annular body 104 having internal annular wall 106 for intimately engaging outer wall 102 of core 100. Helical bore 108 is provided in annular body 104 proximate wall 106 opening through wall 106 (see FIG. 11). Ends 108A and 108B of bore 108 open into openings 110 and 112 at either end of flow restrictor 72' for passing solution from opening 110 through helical bore 108 to opening 112. Because of the intimate contact between outer wall 102 of core 100 and annular inner wall 106, helical bore 108 passes fluid introduced at opening 110 along to opening 112' at a controlled flow rate (dependent on length of helical bore 108 and the diameter of helical bore 108). Helical bore in this embodiment is 20' (about 50 cm.) long and of a diameter of 0.008" (about 0.02 cm.).

Annular body 104 carrying helical bore 108 may be manufactured as follows using injection moulding techniques.

Figure 7:
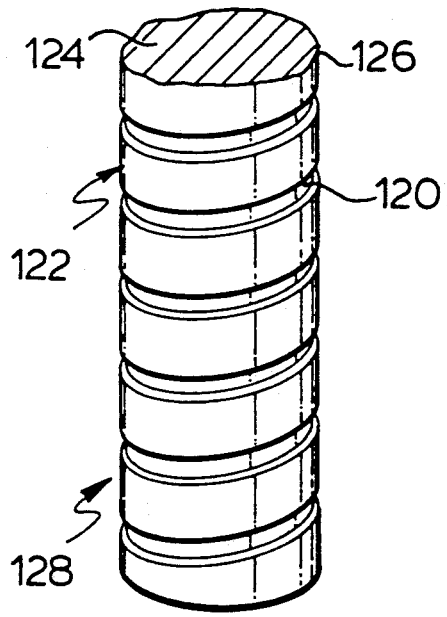
FIGS. 7, 8 and 9 illustrate components suitable for use to manufacture the flow restrictor in FIG. 6.
Figure 8:
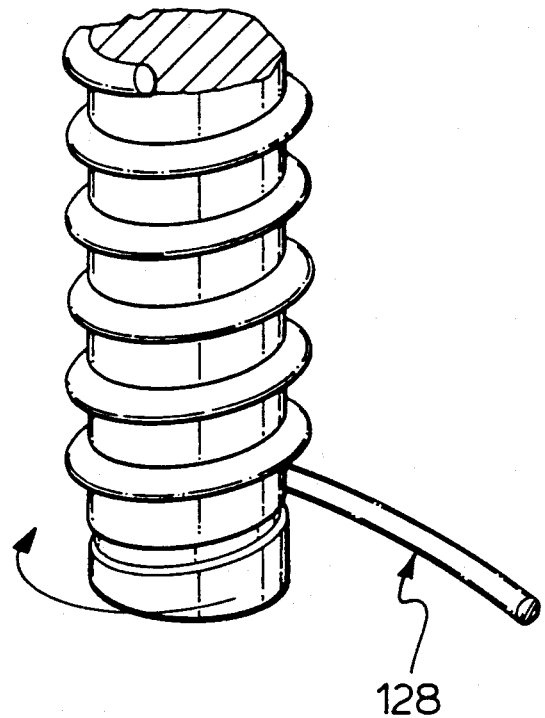
Figure 9:
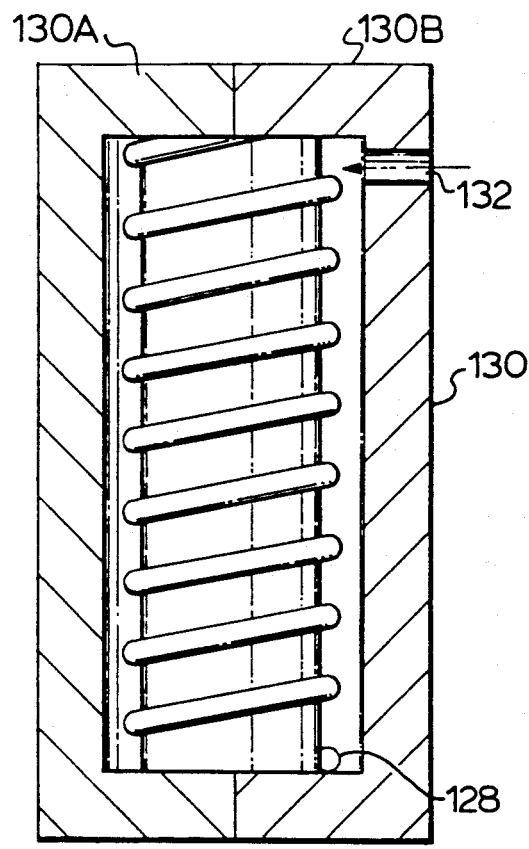
Figure 10:
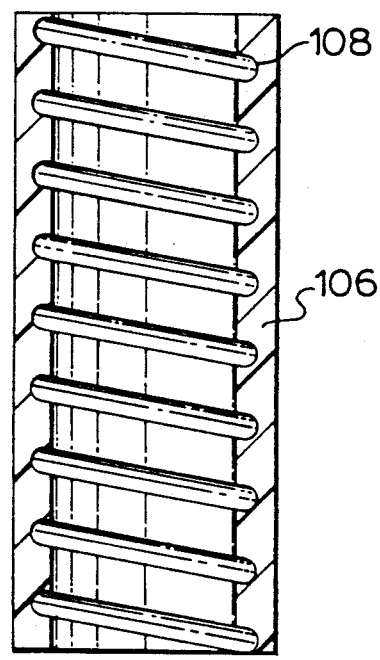
FIG. 10 is a component of the flow restrictor manufactured using the component shown in FIG. 9.

With reference to FIGS. 7-11 flow restrictor 72' may be manufactured by:

(a) providing a helical groove 120 of predetermined length and a predetermined width in the outer surface 122 of core 124 of predetermined length, the helical groove 120 starting at end 126 and continuing to end 128 of core 124 see FIG. 7);

(b) winding 0.008" diameter precision wire 128 in the groove 120 and solder with silver solder (see FIG. 8);

(c) inserting the formed core 124 into two piece (130A and 130B) female mould 130, the interior of which together with formed core 124 for forming similar body 106 with helical bore 108 and injecting liquid transparent plastic moulding material through opening 132, closing opening 132, cooling the mould, separating pieces 130A and 130B, helically unwinding core 124 from formed part 106;

(d) inserting core 100 of same diameter as core 124 and (e) applying end openings 110 and 112' incorporating end caps 110' and 112.

The completed flow restrictor 72' may be used as restrictor 72.

Air Bladder 64 is carried in compartment 58 and contains inlet tubing 140, pressure relief (release) valve 142, pressure gauge 144 and hand pressure pump 146. Air bladder 64 is made of flexible extensible (extendible) rubber like material, (eg. pvc) which when inflated, expands fully so that the rubber like material stretches. As air bladder 64 expands, its volume completely fills compartment 58 stretching walls 36, 38 and 40 of bag 30 exerting pressure on Intravenous bag 62 (previously put into compartment 57). Air bladder 64 is filled to exert a pressure on the walls of the compartment to stretch the walls 36, 38 and 40.

Pressure relief valve 142 is disposed on line 140 and opens to release pressure in the line 140 in excess of a predetermined pressure of example 105 mm Hg.

Hand pump 146 (shown in FIG. 2) is secured to the open end 150 of line 140 and comprises compressible ball 146A (made of rubber or flexible compressible plastic material) both ends comprising bi-directional valves 152A and 152B (patented by Vernay Laboratories under U.S. Pat. Nos. 4,341,239 and 4,434,810). Each valve 152A and 152B opens in both directions at different pressures—to permit air to enter through valve 152A into the volume of ball 146A, when the ball is released after squeezing, then through valve 152B into line when ball 146A is squeezed. When the pressure in the line 140 exceeds a predetermined pressure, the pressure is released through (not only valve 142) but also valves 152B and 152A.

Pressure gauge 144 indicates the pressure in the line (caused by bladder 64 on intravenous bag 62).

An alternate and inexpensive pressure indicator may replace pressure gauge 144 in line 140. With reference to FIGS. 15-21 pressure indicators 142' and 142" are shown, indicator 142' shown in FIGS. 15-17 and indicator 142" is shown in part in FIGS. 18 and 19. Each of the indicators 142' and 142" comprise thick corrugated rubber bellows 160, one end 162 of bellows 160 being open and fitting over raised outlet 164 leading from line 140. The opposite end 165 of bellows 160 is closed. Bellows 160 is carried in an open ended transparent tube 166 in indicator 142' and in closed ended transparent tube 168 in indicator 142". The end of tube 166 and 168 proximate raised outlet 164 are each narrowed to secure end 162 of bellows 160 to raised outlet 164.

Each indicator 142' and 142" carries lines 170 at predetermined levels to indicate pressure. Indicator 142' also carries toggle arm 172 connected to electrical switch 174 to activate a buzzer carried in switch 174 to indicate repressurizing is required when the pressure falls from the pressure indicated by the upper line 170' (e.g. 100 mm Hg.) to the pressure indicated by the lower line (e.g. 95 mm Hg.). In this regard toggle arm rises and falls on bellows 160. When toggle arm 172 falls to line 170", the buzzer is activated.

In operation bellows 160 of indicator 142' elongates (stretches) in tube 166 as the pressure in line 140 increases. Line 170 indicates different pressure readings given by indicator 142'.

Because indicator 142" is closed, indicator 142" will be used to measure higher pressures. In this regard with reference to FIG. 18, indicator 142" is shown with the use of longer bellows 160' shown in FIG. 20. Indicator 142" shown in FIG. 19 employs shorter bellows 160" shown in FIG. 21. As is apparent the volume between bellows end 165 and the closed end of the tube 168, in indicator 142" in FIG. 19 is greater than double the volume between the bellows end 165 and the closed end of tube 168 in indicator 142" in FIG. 18. Thus the indicator in FIG. 19 is more accurate (more than twice the accuracy).

With reference to FIG. 5, because of the fact that air permeable material 60 spaces Intravenous bag 62 from bladder 64, if a leak should occur either by a leak in Intravenous bag 62 as at 62' or by a leak in air bladder 64 as at 64', solution or air (as the case may be) may escape and their loss can be easily detected.

With reference to FIG. 3, cylinder 200 may be used to pressurize bladder 64 through line 140 as required (instead of hand pump 146) still employing pressure relief valve 142.

With reference to FIGS. 12 and 13, it is clear that the use of bladder 202 of the same volume as the Intravenous bag 204, does not provide an infusion pump useable over a long period of time without pumping up the bladder 202. The reader will notice the graph immediately adjacent FIG. 12, shows an immediate drop of the pressure with minimal volume transfused. However, with respect to the infusion device of FIG. 13, it is clear the pressure drops minimally as the same volume is infused. In fact FIG. 14 illustrates how an infusion device 30 can be used continuously to deliver medicine with minimal requirements to pressurize. In this regard, because the infusion device comprises flexible and extensible material, (case or housing), the material that has been stretched, will when fluid has been infused from the intravenous bag, restore to an unstretched (non extended) configuration. Thus minimal pressure decrease would occur thereby maximizing the fluid to be infused with minimal drop in the pressure in the pressure bladder.

As many changes can be made to the invention without departing from the scope of the invention, it is intended that all material contained herein be interpreted as illustrative of the invention and not in a limiting sense.

The embodiments of the invention in which an exclusive property or privilege is claimed are as follows:

1. A portable infusion device which can be user operated almost anywhere for administration of a solution at a substantially steady flow rate from storage, the device comprising in combination a flow restrictor and a propulsion system using a pressure medium carried in a flexible extendible container surrounding the pressure medium and solution for causing the solution to be administered to a patient at a substantially steady rate of flow through the flow restrictor, the volume of the pressure medium being at least about five times the volume of the solution.

2. A portable infusion device for administration of a solution at a substantially steady flow rate from storage, the device comprising a flexible extendible housing enclosing a predetermined volume, the housing for receiving a reservoir (having an outlet) of the solution to be administered under pressure and a pressure bladder comprising a flexible extensible (extendible) container for carrying a pressure medium, the pressure bladder when pressurized being in intimate pressure contact in the housing with the reservoir, the volume of the pressure bladder when pressurized being at least about five times the volume of the reservoir.

3. The infusion device of claim 2 wherein the outlet of the reservoir carries a flow restrictor.

4. A portable infusion device for administration of a solution at a substantially steady flow rate from storage, the device comprising a housing enclosing a predetermined volume, at least one opening through the housing into the volume, the housing of flexible and extendible material, a pressure bladder for being carried within the volume of the housing, the bladder being inflatable within the housing and comprising flexible extendible material, the bladder comprising an inlet for introducing the pressure medium into the bladder for inflating the bladder to a predetermined pressure, pressure release means in communication with the contents of the pressure bladder to ensure the predetermined pressure is maintained and excess pressure is released, the volume of the housing also for receiving a reservoir containing the solution to be administered, the reservoir being made of flexible material, an outlet from the reservoir for administering the solution, the outlet comprising a flow restrictor, the volume cf the bladder being at least about five times the volume of the reservoir.

5. The infusion device of claim 4 wherein the bladder is of flexible and extendible (extensible) material.

6. The infusion device of claim 4 wherein the inlet carries a one-way valve for introducing the pressure medium into the bladder.

7. The infusion device of claim 6 wherein the inlet for introducing the pressure medium, is connected to a pressure pump, hand pump, machine pump, or computer controlled machine pump or any other means for filling the bladder to the desired pressure.

8. The infusion device of claim 6 wherein pressure release means and the one way valve for introducing the pressure medium into the pressure bladder may be incorporated into the same valve, a bi-directional relief valve.

9. The infusion device of claim 4 wherein the flow restrictor is a predetermined length of glass tube having a precise opening therethrough.

10. The infusion device of claim 4 wherein the flow restrictor comprises a helical opening spiralling from one end of a plastic or glass tube to the other.

11. The infusion device of claim 4 further comprising a pressure indicating means comprising a bellows carried within a tube, one end of the bellows in communication with the medium in the pressure bladder whose pressure is to be measured, the other end closed, the tube carrying indicia for indicating the pressure of the pressure medium within the bladder.

12. The infusion device of claim 4 wherein the volume in the housing is lined by porous material (air permeable material).

13. The infusion device of claim 4 wherein the at least one opening through the housing may be closed by a zipper.

14. The infusion device of claim 4 wherein the volume in the housing is divided into two compartments to provide a bladder receiving compartment of the housing and drug reservoir compartment.

15. The infusion device of claim 14 wherein the compartments are separated by air permeable material.

16. The infusion device of claim 4 further comprising a flow indicator secured in communication with the outlet from the reservoir for the passage of solution therethrough.

17. The infusion device of claim 4 wherein the pressure relief valve comprises a whistle for whistling when excess pressure in released.

* * * * *